United States Patent
Rakhimov et al.

(12)

(10) Patent No.: US 6,379,377 B1
(45) Date of Patent: Apr. 30, 2002

(54) USE OF INFRARED RADIATION IN THE TREATMENT OF ONCOLOGICAL DISORDERS

(75) Inventors: Khakim Rakhimovich Rakhimov, deceased, late of Tashkent, by Rustan Khakimovich Rakhimov, legal representative; Nariman Kadyrovich Muratkhodjaev; Vladimir Nickolaevich Kuznetsov, both of Tashkent, all of (UZ)

(73) Assignee: Rustam Khakimovich Rakhimov, Tashkent (UZ)

( * ) Notice: Subject to any disclaimer, the term of this patent is extended or adjusted under 35 U.S.C. 154(b) by 0 days.

(21) Appl. No.: 09/363,985

(22) Filed: Jul. 12, 1999

(30) Foreign Application Priority Data

Jul. 17, 1998 (UZ) .................................. 9800536

(51) Int. Cl.[7] ................................. A61N 5/00
(52) U.S. Cl. .................................. 607/88; 607/100
(58) Field of Search ................. 607/88–89, 90, 607/100; 600/10–11; 128/400, 401

(56) References Cited

U.S. PATENT DOCUMENTS

| | | | | |
|---|---|---|---|---|
| 4,469,103 A | * | 9/1984 | Barrett | 128/400 |
| 4,667,658 A | * | 5/1987 | Guibert | 128/24.1 |
| 4,872,458 A | * | 10/1989 | Kanehira et al. | 128/401 |
| 5,836,999 A | * | 11/1998 | Eckhouse et al. | 607/88 |

FOREIGN PATENT DOCUMENTS

UZ      5636      2/1998

* cited by examiner

*Primary Examiner*—Michael Peffley
*Assistant Examiner*—Pete Vrettakos
(74) *Attorney, Agent, or Firm*—Merchant & Gould, P.C.

(57) ABSTRACT

The invention entitled the use of infrared radiation in the treatment of oncological disorders relates to the field of medicine and can be used for treating oncological disorders. The aim of the invention is to create an effective method of treating oncological disorders that involves exposing the patient to infrared radiation. The aim is achieved by exposing the patient to two kinds of infrared radiation, first to pulse infrared radiation with a wavelength of 16 to 16.25 micron, that consists of two short powerful pulses with an intensity up to 320 W/cm$^2$, lasting 10–12 microseconds each, and following each other, and then to infrared radiation with a wavelength corresponding to the body's intrinsic infrared radiation. The exposure to pulse infrared radiation is done first generally, then locally. The exposure to infrared radiation with a wavelength corresponding to the body's intrinsic infrared radiation is also done first generally, then locally. The sites on the patient's body to be exposed to infrared radiation topically are determined by means of electroacupuncture diagnostics according to Voll. The number of sessions and the length of exposure to pulse infrared radiation, as well as the number of sessions and the length of exposure to radiation with a wavelength corresponding to the body's intrinsic infrared radiation, are determined by means of electroacupuncture diagnostics according to Voll.

7 Claims, No Drawings

USE OF INFRARED RADIATION IN THE TREATMENT OF ONCOLOGICAL DISORDERS

FIELD OF THE INVENTION

The invention relates to medicine and can be used for treating oncological disorders.

BACKGROUND OF THE INVENTION

The invention conceptually closest to this one is the 'Method of treating patients' IPC[6] A61B5/04 set out in UZ patent #5636 (application IHDP 9800073.1 of Feb. 3, 1998) published in 1999, that consists of a series of sessions of noncontact treatment and diagnosis of the entire organism, with the patient exposed to infrared (IR) radiation at a wavelength corresponding to that of the body's intrinsic infrared radiation and at a power no less than 5 W, for a number of sessions with a total duration no less than 30 minutes, and the diagnosis consisting of a clinical examination and electroacupuncture diagnosis according to Voll (EAV).

SUMMARY OF THE INVENTION

The method described stimulates and activates the natural metabolic processes in the body, thereby raising the immune status and having an overall therapeutic effect on it. The shortcoming of the method is that it cannot be used to treat oncological disorders. The aim of the present invention is to create an effective method of treating oncological disorders, that involves exposing the patient to infrared radiation. To achieve the aim, the method of treating patients that includes exposing the body to infrared radiation with a wavelength corresponding to the body's intrinsic infrared radiation involves exposing the patient to two kinds of infrared radiation, first to pulse infrared radiation with a wavelength of 16 to 16.25 micron that consists of two short powerful pulses with an intensity up to 320 W/cm$^2$, lasting 10–12 microseconds each, and following each other, and then to infrared radiation with a wavelength corresponding to the body's intrinsic infrared radiation. The exposure to pulse infrared radiation is first done generally, then topically. The exposure to infrared radiation with a wavelength corresponding to the body's intrinsic infrared radiation is also first done generally, then topically. The sites to be exposed topically to infrared radiation are determined by means of EAV. The number of sessions and the length of exposure to pulse infrared radiation and the number of sessions and the length of exposure to radiation with a wavelength corresponding to the body's intrinsic infrared radiation are determined by means of EAV.

DETAILED DESCRIPTION OF THE INVENTION

Pulse infrared radiation can be generated by a special RC lamp coated with a special ceramic material. The ceramic material capable of emitting such pulse infrared radiation with a wavelength of 16 to 16.25 micron is disclosed in UZ patent #5224 (application IHDP 9700645.1 of Jul. 25, 1997) and contains the following ingredients, wt %:

| | |
|---|---|
| lanthanum aluminate | 0.5–10.0 |
| yttrium chromite | 0.5–3.0 |
| magnesium chromite | 1.0–15.0 |
| cerium dioxide | 0.1–1.0 |
| zirconium dioxide | 0.5–5.0 |
| lanthanum chromite | the rest |

RC-line emitters—RC lamps coated with a special ceramic material—are used both topically and generally. The general RC emitter is intended to irradiate the whole surface of the patient's body, whereas the topical RC emitter, to irradiate organs or their parts affected by cancer.

The principle of treating cancerous growths in the patient's body with pulse infrared radiation with a wavelength of 16 to 16.25 micron, that consists of two short powerful pulses is as follows:

According to modern knowledge of the mechanism of developing cancer, free radicals are thought to play a crucial role, in view of their importance to the major cell components.

A free radical is an atom or molecule that has an unpaired electron in the outer orbital. It is very chemically active and tends to extract from its surroundings another electron capable of recombination in order to create a stable electron pair. The molecules involved in the process in turn become active, since now they have an uncoupled, highly active electron.

The presence of such electrons is a precondition to a chain reaction. In the absence of a biological compound that can quickly eliminate free radicals, or in the presence of radicals with high activation energy, the damage to the cell becomes permanent. In norm, free radicals are produced in small amounts in the course of some physiological processes.

An important consideration is that the activation energy of radicals is extremely high and, as a result, the growth of cancerous cells becomes uncontrollable. In this case it becomes imperative to find a way of intervening in the process in order to eliminate the free radicals.

In a cancerous cell the charge of the active part responsible for cell growth and the re-combination of the radical after it has performed its functions is divided, which makes it difficult or impossible to eliminate free radicals by means of antioxidants. For this same reason the activation energy of such radicals is also much higher than that of normal ones.

The RC lamp is a universal eliminator of free radicals that have high activation energy.

The mechanism of action of the pulse infrared radiation generated on switching the RC lamp on is to localize the charge to the active point, thereby raising the reactive capacity of the radical to be eliminated, and then to make it enter into the reaction of elimination.

The pulse radiation generated on switching the RC lamp on is made up of two short powerful pulses with an intensity of up to 320 W/cm$^2$, lasting 10 to 12 microseconds each, and following each other. Each pulse is generated in its own waveband and, accordingly, has its intrinsic quantum energy. The first localizes the divided radical charge, and the second makes it disappear through recombination in resonance.

The treatment of patients is carried out in the following manner:

First, an overall diagnosis of the patient is conducted, which includes a routine examination and EAV, which consists of measuring the biophysical properties of the body's reflexogenic points, that is, the electrical conductivity of the points by means of EAV using, e.g., a device EAV DIAGNOST-1 made in Germany.

Points are determined that have a potential lower than the 'norm corridor' by EAV and the pathology pinned down. On the basis of the diagnosis results, optimal sites are determined for exposure to infrared radiation.

Next the patient is exposed to the RC emitter, first generally, then topically, with the effect on the malignancies exerted by the pulse radiation with a wavelength of 16 to 16.25 micron, that consists of two short powerful pulses following each other. The general RC emitter is intended to irradiate the whole surface of the patient's body; it is placed 80–100 centimetres (cm) above the couch and runs its entire length. For treatment, the patient lies down in a prone position, receives the prescribed dose of radiation, then turns over and receives another dose. The duration of a session depends on the patient's status and is selected on an individual basis by means of EAV, the minimum being 30 seconds in the prone position and 30 seconds in the supine position, and the maximum, 5 minutes in either position (a total of 10 minutes per session). The maximal number of exposures to the general emitter per day is twice (in the morning and evening).

The topical RC emitter is intended to directly irradiate the organs or their parts affected by cancer. The emitter is placed at a distance of 20 to 30 centimetres from the surface of the patient's body and its position relative to the affected region is changed 3 to 5 times during the session so that it is irradiated at different angles and on different sides. The posture taken up by the patient depends on the region affected. The duration of the session depends on the patient's status and is determined by means of EAV, the minimum being 1 to 3 minutes for the region affected (20 to 35 seconds in each projection), and the maximum, 20 minutes.

This is followed by the patient being exposed to a KD-4 emitter, first generally, and then, if necessary, topically.

The KD-4 emitter generates continuous infrared radiation whose wavelength corresponds to the wavelength of the body's intrinsic radiation and occupies the range of 9 to 10 micron; it is intended to normalize metabolism (that is, to normalize the rates of biochemical reactions) by irradiating the surface of the patient's body.

The general KD-4 emitter is placed 80 to 100 centimetres above the surface of the couch and runs its entire length. Treatment is done by the patient lying down in a prone or supine position (it does not matter which). The duration of a session depends on the patient's status and is selected on an individual basis by means of EAV, the minimum being 3 minutes, and the maximum 15 minutes. The maximal number of exposures to the general KD-4 emitter is twice a day (in the morning and evening). The topical KD-4 emitter is intended to normalize the immune status.

The sites receptive to the radiation from the emitter are the head (in the parietal and occipital regions) and the regions of the $7^{th}$ cervical vertebra, the heels, and the upper thorax (the thymus—mainly in children). The sensitivity of the sites and the duration of exposure to the emitter are determined by means of EAV, the minimal length of exposure being 30 seconds, the maximal length 15 minutes, and the maximum number of sessions per day, three times.

The duration of exposure to the emitters is determined by testing by means of electroacupuncture and depends on the patient's status and the initial status of the affected organ or its part.

The whole procedure is as follows: first the biologically active point (BAT) potential is measured at the control point on the meridian of vasoparenchymatous epithelial degeneration (VPED) or the point reflecting the function of the affected organ or its part, next the emitter is placed near the affected region, after which the value reflecting the activity of processes at the point begins to approach the norm and, after reaching a plateau at a certain level, falls off again. Exposure to the emitter is stopped as the reading begins to fall below the norm. After the treatment is concluded, a final diagnosis is made.

Treatment can be conducted for both in- and outpatients, or a patient can come for treatment when a session is due.

Contraindications: alcohol intake, as well as the infriction of alcohol and alcohol-based compound, 14 days before, during, and 14 days after, treatment. There are no other contraindications.

The course of treatment consists of 6 to 60 sessions. 35 people have been treated by the above method, and all the results have been favorable.

EXAMPLE 1

Patient Alla A., female, aged 39.

Clinical diagnosis: bilateral diffuse fibrocystic mastopathy.

Case history: according to her, the growth on the right has been present for 10 years, that on the left, for 1 year. She is observed at the cancer hospital in Moscow with a diagnosis of fibrocystic mastopathy. She was offered an operation, which she has refused.

The data of an examination before treatment:

Blood pressure 100/65 mm Hg, heart rate 88 beats a minute, complete blood count: hemoglobin 90 g/l, erythrocytes 3.0×1012, leukocytes 7.2×109, eosinophils 2, erythrocyte sedimentation rate 28 mm/h.

The data of instrument examinations: ultrasonic scanning of Jan. 6, 1998 revealed small cysts 0.5 cm in diameter superimposed on fibrous cords up to 1 cm thick. On the frontal surface of the left mammary gland there is a cavity 2.2 cm in diameter with clearly defined contours and homogeneous liquid contents.

Measuring the acupuncture point potentials by means of EAV revealed deviations from the norm (which is 50–70 arbitrary units) on the VPED meridian: 34 on the right and 28 on the left.

Before giving treatment, the state was determined of the functional activity of the pancreas, adrenals, sympathetic and parasympathetic nervous systems.

Treatment was done in the following manner:

The patient was laid on the couch under the RC emitter, first in a prone position, then in a supine position. The length of exposure on the first day was determined by means of EAV and was 8 minutes.

On the second day it was half that time, to prevent intoxication manifestations. On the third day it was ⅔ of the maximal time. On the fourth day it was that of the first day, and then the treatment was repeated as described.

During treatment the maximal length of exposure was repeatedly determined by means of EAV. The RC emitter was followed by the general KD-4 emitter. In this case, too, the length of exposure was determined by means of EAV and was 10 minutes.

After completing the general sessions the patient was prescribed the RC emitter to irradiate the region of each mammary gland for five minutes in three projections, i.e. at different angles, which totaled 15 minutes.

The KD-4 emitter was used to irradiate the pancreatic region on days when testing by means of EAV revealed that the potentials on the points of secretory activity were below normal.

The entire treatment ran to 55 sessions, which were carried out daily.

The treatment result: stabilization of the process.

The data of an examination after treatment:

Blood pressure 110/70 mm Hg, heart rate 76 beats a minute, complete blood analysis: hemoglobin 110 g/l, erythrocytes $3.8 \times 10^{12}$, leukocytes $7.2 \times 10^9$, eosinophils 1, erythrocyte sedimentation rate 14 mm/h.

Ultrasonic scanning revealed no cysts on the right, and only two cysts on the left measuring 0.2 cm and 0.4 cm. Scanning conducted monthly has revealed no recurrences.

After completing the treatment the EAV potentials are back to normal.

EXAMPLE 2

Patient Alexander K., male, aged 47.

Clinical diagnosis: lower lip squamous cell carcinoma.

Case history: in 1997 he underwent radiation therapy to treat lower lip carcinoma, after which a post-radiation scar formed. In January 1998 there was a recurrence of the condition, and the patient went for consultation to the., Tashkent Region Cancer Hospital and the city cancer hospital, where a diagnosis was made of a recurrence of lower lip carcinoma.

The data of an examination before treatment:

Blood pressure 130/85 mm Hg, heart rate 70 beats a minute, complete blood analysis: hemoglobin 98 g/l, erythrocytes $3.0 \times 10^{12}$, leukocytes $7.2 \times 10^9$, eosinophils 2, erythrocyte sedimentation rate 30 mm/h.

The data of instrument examinations: hystological analysis #553 of Nov. 3, 1997 revealed lower lip squamous cell carcinoma. In the right part of the lower lip there was a crater-like ulcer measuring 10×10 mm.

Measuring the potentials by means of EAV detected deviations from the norm (which is 50–70 arbitrary units) on the skin meridian—30 on the right and 28 on the left—and on the VPED meridian—36 on the right and 32 on the left.

The treatment was done in the following manner:

The sessions were carried out daily. The patient was laid on a couch under the RC emitter, first in a prone position, then in a supine one. The length of exposure for the first day was determined by means of EAV and was 14 minutes. On the second day it was half the time prescribed for the first day, and on the third, ⅔ of the maximum. On the fourth day the length of exposure was that of the first day, and the treatment was continued in this manner.

During treatment the maximal length of exposure was repeatedly determined by means of EAV. Exposure to the general RC emitter was followed by that of the ulcer region on the lower lip to the topical RC emitter in five projections, i.e. at different angles. This was done 5 times a day throughout the course. The maximal length of exposure was determined by means of EAV. The length of the first session was 2 minutes, that of the second, 3 minutes, that of the third, 4 minutes, that of the fourth, 5 minutes, and that of the fifth, 7 minutes.

The length of exposure was varied so that no adaptation would develop to a stimulus of the same strength.

At the conclusion of the course, daily exposure was administered to the topical KD-4 emitter, which was positioned so as to irradiate the heel region, since that area had been found by testing to be sensitive to the emitter. The length of exposure was 10 minutes.

The course took 25 days without interruption.

The treatment results: the lower lip acquired well-defined contours and was completely cleansed of affected tissue; a small scar was left where the ulcer had been.

The data of an examination after treatment:

Blood pressure 120/75 mm Hg, heart rate 70 beats a minute, complete blood count: hemoglobin 110 g/l, erythrocytes $3.8 \times 10^{12}$, leukocytes $7.0 \times 10^9$, eosinophils 1, erythrocyte sedimentation rate 19 mm/h.

EXAMPLE 3

Patient Lyudmila P., female, aged 68.

Clinical diagnosis: lower lip squamous cell carcinoma of the $3^{rd}$ degree, the $2^{nd}$ clinical group.

Case history: she has been ill for several months; after examining her at the institute of cancer research and radiation therapy, the above diagnosis was made. The patient has refused special treatment.

The data of an examination before treatment:

Blood pressure 140/90 mm Hg, heart rate 82 beats a minute, complete blood analysis: hemoglobin 78 g/l, erythrocytes $3.2 \times 10^{12}$, leukocytes $6.8 \times 10^9$, eosinophils 3, erythrocyte sedimentation rate 57 mm/h.

The data of instrument examinations: histological studies have revealed moderately differentiated squamous cell carcinoma.

In measuring the potentials by means of EAV there was an indicator drop on the VPED meridian: 20 on the left and 22 on the right, the norm ranging from 50 to 70.

The treatment was done in the following manner:

The patient was laid on a couch under the RC emitter, first in a prone position, then in a supine one. The length of the first exposure was determined by means of EAV and was 6 minutes. On the second day it was half that of the first day, to prevent any intoxication phenomena, that is, 1.5 minutes in each position.

On the third day the length of exposure was ⅔ of the maximum (2 minutes in each position). On the fourth day the length of exposure was that of the first day, and the treatment was done in this manner.

During treatment the maximal length of exposure was repeatedly determined by means of EAV. Exposure to the general RC emitter was followed by the topical emitter irradiating the ulcer region on the lower lip in five projections, that is, at various angles. This was done three times a day throughout the course of therapy.

The maximal length of exposure was determined by means of EAV. The first session lasted 2 minutes, the second, 4 minutes, and the third, 5 minutes.

At the conclusion of treatment the topical KD-4 emitter was positioned so as to irradiate the region of the heels, since it was that site that proved sensitive to the emitter. The length of exposure was 10 minutes.

The course of treatment lasted 61 days without interruption.

Treatment results: the lower lip became clearly, defined and completely purged of abnormal tissue; the lymph nodes cannot be palpated; the EAV potentials are back to normal.

The data of an investigation after treatment:

Blood pressure 130/80 mm hg, heart rate 74 beats a minute, complete blood count: hemoglobin 110 g/l, erythrocytes $3.5 \times 10^{12}$, leukocytes $4.8 \times 10^9$, eosinophils 2, erythrocyte sedimentation rate 23 mm/h.

We claim:

1. A method of treating patients comprising: exposing the patient to infrared radiation for a predetermined number of sessions at a wavelength corresponding to that of the body's intrinsic infrared radiation, wherein the patient is exposed to two kinds of infrared radiation, first to pulse infrared radiation with a wavelength of 16 to 16.25 micron and including two short powerful pulses with an intensity up to 320 W/cm$^2$, lasting 10–12 microseconds each, and following each other, and then to infrared radiation with a wavelength corresponding to the body's intrinsic infrared radiation.

2. A method of treating according to claim 1, wherein exposure to pulse infrared radiation is done first generally, then topically.

3. A method of treating according to claim 1, wherein exposure to infrared radiation with a wavelength corresponding to the body's intrinsic infrared radiation is done first generally, then topically.

4. A method of treating according to claim 1, wherein the sites on the patient's body to be irradiated topically are determined by means of electroacupuncture diagnostics according to Voll.

5. A method of treating according to claim 1, wherein the number of sessions and the length of exposure to pulse infrared radiation, as well as the number of sessions and the length of exposure to infrared radiation with a wavelength corresponding to the body's intrinsic infrared radiation, are determined by means of electroacupuncture diagnostics according to Voll.

6. A method of treating according to claim 2, wherein the sites on the patient's body to be irradiated topically are determined by means of electroacupuncture diagnostics according to Voll.

7. A method of treating according to claim 3, wherein the sites on the patient's body to be irradiated topically are determined by means of electroacupuncture diagnostics according to Voll.

* * * * *